United States Patent [19]
Sola

[11] Patent Number: 5,201,770
[45] Date of Patent: Apr. 13, 1993

[54] FEMORAL INSERT FOR TOTAL HIP PROSTHESIS

[76] Inventor: Enrique P. Sola, C. Coso, 77, 50001 Zaragoza, Spain

[21] Appl. No.: 811,316

[22] Filed: Dec. 20, 1991

[30] Foreign Application Priority Data

Jan. 2, 1991 [ES]  Spain ................................. 9100003

[51] Int. Cl.⁵ ............................................. A61F 2/36
[52] U.S. Cl. ........................................ 623/23; 623/18
[58] Field of Search ..................... 623/23, 22, 18, 16

[56] References Cited

U.S. PATENT DOCUMENTS

| 4,287,617 | 9/1981 | Tornier | 623/23 |
| 5,092,899 | 3/1992 | Forte | 623/23 |

FOREIGN PATENT DOCUMENTS

| 2627380 | 8/1989 | France | 623/18 |
| 2636837 | 3/1990 | France | 623/22 |
| 2639821 | 6/1990 | France | 623/22 |

Primary Examiner—Ronald Frinks
Attorney, Agent, or Firm—Steinberg & Raskin

[57] ABSTRACT

A novel femoral insert for total hip prosthesis is disclosed. The insert lacks any widening on the trochantereal part and the internal longitudinal hollow has a constant diameter throughout its entire length. One embodiment includes an inclined rib on the trochantereal. The insert has elasticity and power of recovery when it is pressed laterally in the direction of the closing of a longitudinal slot of the insert.

3 Claims, 2 Drawing Sheets

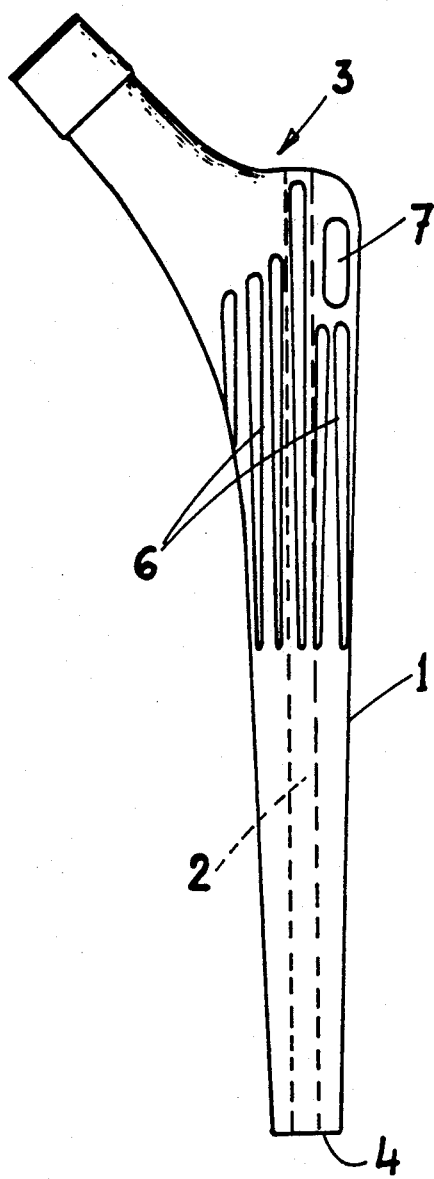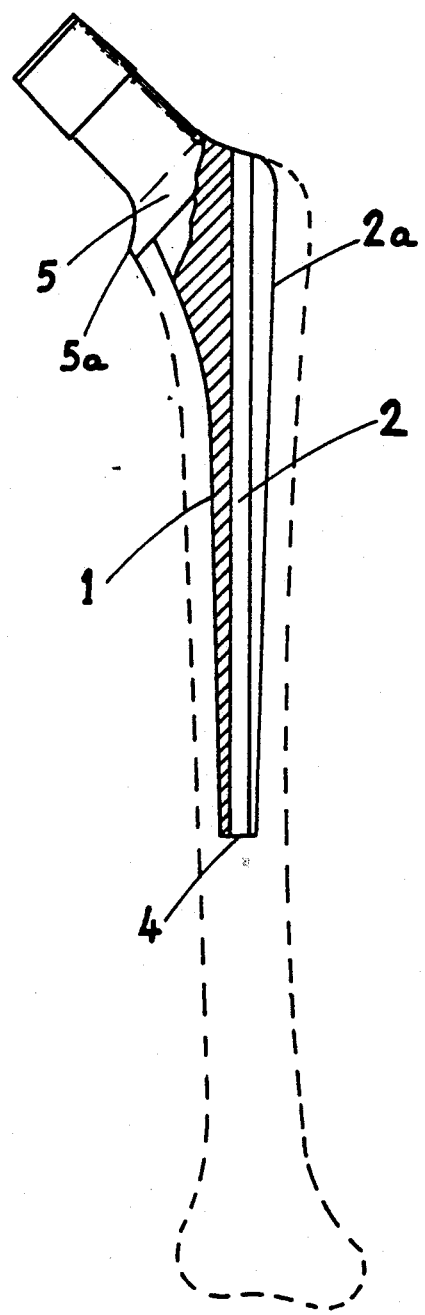

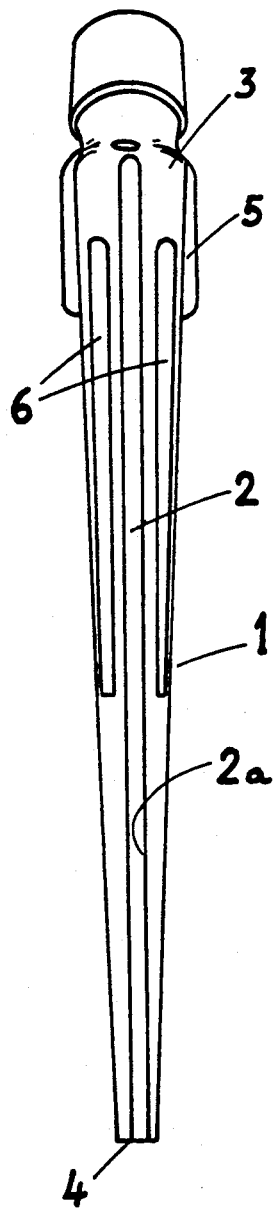
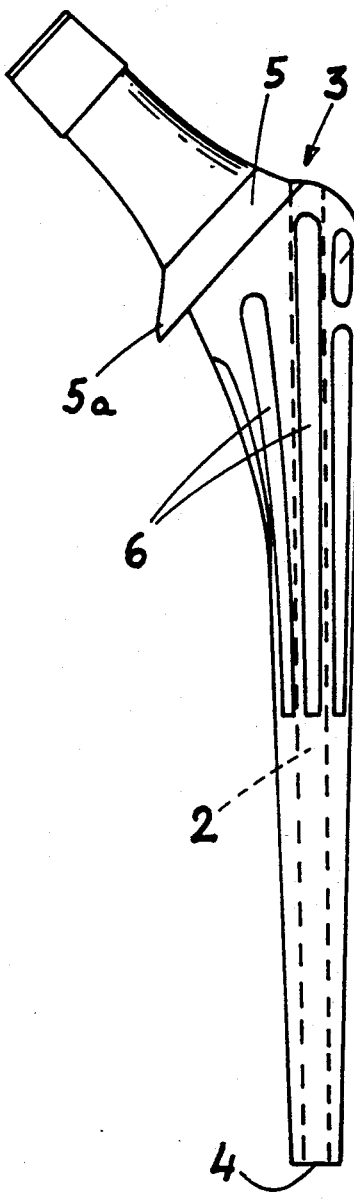
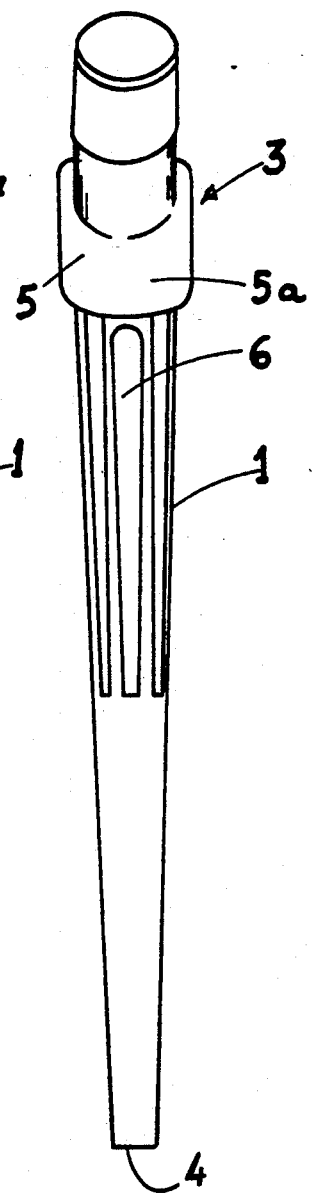
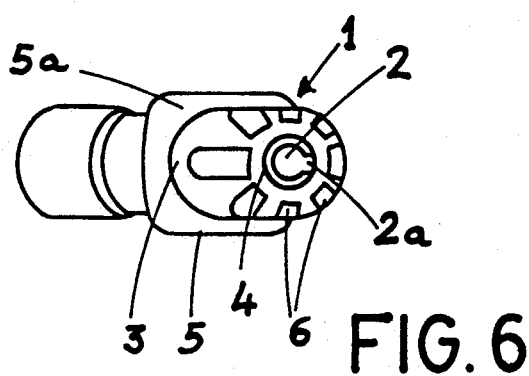

FEMORAL INSERT FOR TOTAL HIP PROSTHESIS

The present invention refers to a femoral insert for total hip prosthesis, thanks to which notable improvements are achieved in relation to the inserts of this type known to date. Said improvements involve simplification of the operation which has to be carried out on the patient in order to implant the insert and also of the fitting of a pin inside the insert in the event of a hypothetical fracture of the femur once the insert has been fitted.

BACKGROUND OF THE INVENTION

Known in the art of prostheses are femoral inserts for total hip prosthesis, which inserts present great difficulty when it comes to extraction thereof, due to the special characteristics of their mechanism for anchorage in the bone and due also to their solid configuration, which prevents reduction of their diametral width.

In order to avoid the disadvantages of this type of insert, the holder of the present invention, Dr. Enrique Pelegrin Solá made a new insert, which is the object of Spanish Utility Model U 8600323, whose fundamental characteristics are as follows: the presence of external longitudinal ribs; the hollow configuration of the insert, due to the fact that it possesses a cavity running along its entire length; and the presence of a trochantereal part which is notably thicker than the rest, provided with notches for the coupling of a mechanical compressor device for reduction of the cross-section of the entire insert in order to facilitate the extraction thereof.

Experience has nevertheless shown that it is possible to improve the characteristics of the insert object of said Spanish Utility Model U 8600323, and in consequence a new insert has been designed, the characteristics of which are the object of the present invention.

DESCRIPTION OF THE INVENTION

The femoral insert for total hip prosthesis is of the type which presents a hollow running through its entire length, with a longitudinal slot communicating the hollow and the exterior of the insert, provided on the trochantereal part with lateral depressions close to the edges of the groove. On the basis of this embodiment, the insert is characterized essentially in that the longitudinal groove has a uniform diameter throughout its entire length. Moreover, the upper part of the insert, corresponding to the trochantereal zone, lacks any pronounced thicker sections.

In an optional embodiment, the insert presents around the trochantereal part an outcrop in the form of a rib in inclined position with respect to the longitudinal axis of the insert. This outcrop projects very little in relation to the lateral surface of the insert and rather more in relation to the front part of same.

The external surface of the insert presents longitudinal slots which run along approximately the upper half of the height of the insert.

The insert presents sufficient elasticity to allow it to deform temporarily by means of lateral pressure in the direction of closing the longitudinal slot of the hollow and to recover its position again when said lateral pressure ceases.

BRIEF DESCRIPTION OF THE DRAWINGS

For a better understanding of all that is described in the present specification, some drawings are attached in which, solely by way of example, a practical case of embodiment of the femoral insert is shown.

In said drawings

FIG. 1 is a side elevation view of the insert without a rib on the trochantereal part;

FIG. 2 is a longitudinal section view of the insert provided with an inclined rib around the trochantereal part, constituting a calcar support once the insert has been placed inside the bone;

FIG. 3 is an elevation view of the side on which the groove is open on an insert;

FIG. 4 is a side elevation view of the same insert;

FIG. 5 is an elevation view of the same insert, seen from the opposite side with respect to the view of figure 3; and FIG. 6 is a plan view from the lower end of the insert.

DESCRIPTION OF A PREFERRED EMBODIMENT

The femoral insert in question comprises a piece -1- of a hard biocompatible material, whether plastic or metal. The external surface of the piece -1- may be provided with a rough coating of granular, filamentary or any other nature, in order to facilitate regeneration of tissues involved, basically osseous tissue. The piece -1-is provided with a longitudinal hollow -2-, in communication with the exterior by means of a longitudinal slot -2a- or at any other appropriate zone, opened in its rear side, running from the trochantereal zone -3- to the lower end -4- of the insert. The piece -1- diminishes progressively in width towards its lower end.

A description has been provided so far of already known aspects of the femoral insert.

The essential characteristics of the femoral insert consist in the absence of thick outcrops on the trochantereal part -3- (FIG. 1), or, at most, in the presence of an inclined rib -5- around it —FIGS. 2, 3, 4 and 5 - which projects slightly with respect- to the surface of the side walls of the zone -3- and which at the frontal part forms a more pronounced outcrop -5a-.

Another notable characteristic of the femoral insert consists in the hollow -2- having a uniform diameter throughout its entire length (FIG. 2).

On the exterior surface of the insert -1- there are longitudinal slots -6- which take in only the upper half of the total height of the insert.

In the zone -3- there are two lateral depressions -7- near to the slot -2a-, or in any other appropriate zone, for the placing of an instrument intended to apply pressure on the zone -3- in a direction which brings together the edges of the slot in order to facilitate driving of the insert into the bone.

From all that has been set forth and through observation of the drawings, the advantages presented by the insert in question compared to other preceding embodiments may be appreciated.

In the first place, the absence of a wide head at the upper or trochantereal part be stressed. Thanks to this, fitting of the insert requires a surgical operation through the lateral part of the limb, instead of an operation through the rear part. This surgical operation through the lateral part is less traumatic and easier to perform.

Furthermore, the absence of the aforesaid head permits elimination of a smaller zone -of- the affected bone, thus simplifying the intervention and facilitating recovery of the affected limb.

In the version illustrated in FIGS. 2 to 5, in which the insert presents a rib -5- which projects very little on the lateral sides, surgical intervention is also viable by lateral access, thanks to the scant relief of the rib in question. This rib provides a calcar support on the bone, cut in an inclined manner, as illustrated in FIG. 2.

When the insert lacks a calcar support (figure 1), the insert is fitted by pressing on it laterally in a direction which brings together the edges of the slot -2a- so that, once placed inside the bone, it recovers its position on ceasing of the lateral pressure, thus allowing the insert to be perfectly secured inside the bone.

Thanks to the uniformity of the diameter of the hollow -2- throughout its entire length, when it is necessary to fit a pin inside the insert, due to breakage of the bone arising once the insert has been fitted, the pin is perfectly tight throughout its length, with no lateral displacements of same occurring.

Independent of the object of the invention shall be the materials used in manufacturing of the femoral insert, shapes and dimensions of same and all accessory details which might be presented, as long as they do not affect its essential nature.

I claim:

1. Femoral insert for total hip prosthesis, of the type which is of hollow configuration, said insert comprising
   a piece having an upper part, an exterior and a longitudinally extending lower section, said longitudinally extending lower section having an interior and a back side,
   a longitudinal hollow running in said interior of said longitudinally extending section, said longitudinal hollow having a uniform diameter,
   a longitudinal slot placed on said exterior of said piece on said back side, said longitudinal slot having edges, said longitudinal hollow connected to said exterior of said piece by means of said longitudinal slot,
   lateral depressions on said upper part near said edges of said longitudinal slot,
   said upper part of said insert lacking pronounced thicker sections.

2. Femoral insert for total hip prosthesis, as claimed in claim 1, further comprising additional longitudinal slots on said exterior of said piece, said additional longitudinal slots extending along an upper half of said longitudinally extending section.

3. Femoral insert for total hip prosthesis, as claimed in claim 1, wherein said insert is made of a material having sufficient elasticity such that said insert is deformable temporarily by means of lateral pressure applied in a direction to close said longitudinal slot of said longitudinal hollow.

* * * * *